US00PP31572P2

(12) United States Plant Patent
Winslow et al.

(10) Patent No.: US PP31,572 P2
(45) Date of Patent: Mar. 17, 2020

(54) ***CALIBRACHOA* PLANT NAMED 'BALCABORIM'**

(50) Latin Name: ***Calibrachoa* x *hybrida***
Varietal Denomination: Balcaborim

(71) Applicant: Ball Horticultural Company, West Chicago, IL (US)

(72) Inventors: Benjamin K. Winslow, Austin, TX (US); Laura L. Masor, Grover Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/501,954

(22) Filed: Jul. 10, 2019

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC ..... A01H 5/02; A01H 6/82
See application file for complete search history.

*Primary Examiner* — Annette H Para
(74) *Attorney, Agent, or Firm* — Audrey Charles

(57) ABSTRACT

A new and distinct cultivar of *Calibrachoa* plant named 'Balcaborim', characterized by its deep reddish-orange colored flowers, medium green-colored foliage, and moderately vigorous, mounded-trailing growth habit, is disclosed.

1 Drawing Sheet

Latin name of genus and species of plant claimed: *Calibrachoa* x *hybrida*.

Variety denomination: 'Balcaborim'.

BACKGROUND OF THE INVENTION

The present invention relates to a new and distinct cultivar of *Calibrachoa* plant botanically known as *Calibrachoa* x *hybrida* and hereinafter referred to by the cultivar name 'Balcaborim'.

The new cultivar originated in a controlled breeding program in Arroyo Grande, Calif. during March 2016. The objective of the breeding program was the development of *Calibrachoa* cultivars with attractive flower coloration, and a moderately vigorous, mounded-trailing growth habit.

The new *Calibrachoa* cultivar is the result of cross-pollination. The female (seed) parent of the proprietary *Calibrachoa* x *hybrida* breeding selection coded JJ 214R, not patented, characterized by its medium scarlet-colored flowers, medium green-colored foliage, and vigorous, mounded growth habit. The male (pollen) parent of the new cultivar is the proprietary *Calibrachoa* x *hybrida* breeding selection coded 13601-1, not patented, characterized by its medium orange-colored flowers having a red center, medium green-colored foliage, low growth vigor, and a compact-mounded growth habit. The new cultivar was discovered and selected as a single flowering plant within the progeny of the above stated cross-pollination during August 2016 in a controlled environment in Arroyo Grande, Calif.

Asexual reproduction of the new cultivar by terminal stem cuttings since August 2016 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcaborim' as a new and distinct cultivar of *Calibrachoa* plant:

1. Deep reddish-orange colored flowers;
2. Medium green-colored foliage; and
3. Moderately vigorous, mounded-trailing growth habit.

Plants of the new cultivar differ from plants of the female parent primarily in having a different flower color and less vigorous growth habit. Plants of the new cultivar differ from plants of the male parent primarily in having a different flower color and more vigorous growth habit.

Of the many commercially available *Calibrachoa* cultivars, the most similar in comparison to the new cultivar is CABARET Orange Balcaborg', U.S. Plant patent application Ser. No. 14/998,873, now abandoned. However, in side-by-side comparisons, plants of the new cultivar differ from plants of 'Balcaborg' in at least the following characteristics:

1. Plants of the new cultivar have a flower color that is a darker reddish-orange color than plants of 'Balcaborg';
2. Plants of the new cultivar have a smaller corolla diameter than plants of 'Balcaborg'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balcaborim'. The plants were approximately 7 months old and grown in 3-gallon containers in an outdoor nursery environment in West Chicago, Ill. for approximately 4 months. Treatments are described below in the Detailed Botanical Description.

DETAILED BOTANICAL DESCRIPTION

Figure 1:
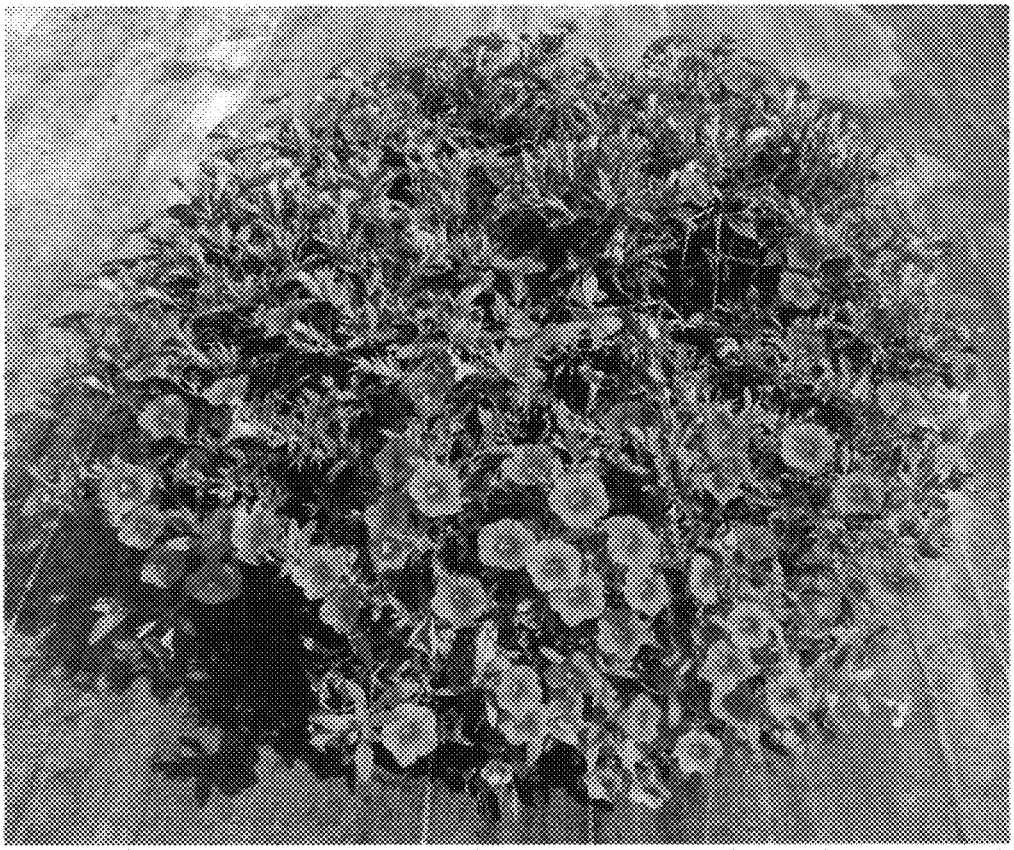
FIG. 1 illustrates a side view of the overall growth and flowering habit of 'Balcaborim'.
Figure 2:
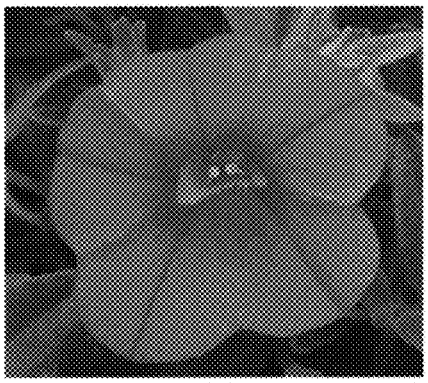
FIG. 2 illustrates a close-up view of an individual flower of 'Balcaborim'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in September 2018 under natural light conditions in West Chicago, Ill.

The following descriptions and measurements describe plants produced from cuttings from stock under conditions comparable to those used in commercial practice. The plants were approximately 7 months old and grown in 3-gallon containers in an outdoor nursery environment in West Chicago, Ill. for approximately 4 months. Plants were given two pinches, the first at 3 weeks after cuttings were stuck and a second approximately 3 weeks later. Plants were treated with plant growth regulators of Daminozide at 2500 ppm and Chlormequat chloride at 750 ppm approximately 4 weeks after cuttings were stuck. Measurements and numerical values represent averages of typical plants.

Botanical classification: *Calibrachoa* x *hybrida* 'Balcaborim'.

Parentage:

*Female parent.*—Proprietary *Calibrachoa* x *hybrida* breeding selection coded JJ 214R, not patented.

*Male parent.*—Proprietary *Calibrachoa* x *hybrida* breeding selection coded 13601-1, not patented.

Propagation:

*Type cutting.*—Terminal stem.

*Time to initiate roots.*—Approximately 6 to 8 days.

*Time to produce a rooted cutting.*—Approximately 21 to 28 days.

*Root description.*—Fibrous.

*Rooting habit.*—Freely branching.

Plant description:

*Commercial crop time.*—Approximately 6 to 9 weeks from a rooted cutting to finish in a 10 cm pot.

*Growth habit and general appearance.*—Moderately vigorous, mounded-trailing.

*Size.*—Height from soil level to top of plant plane: Approximately 20.0 cm. Width: Approximately 53.0 cm.

*Branching habit.*—Freely branching, pinching enhances basal branching. Quantity of main branches per plant: Approximately 4.

*Branch.*—Strength: Moderate. Length: Approximately 32.0 cm. Diameter: Approximately 2.0 mm. Length of central internode: Approximately 2.5 cm. Texture: Densely pubescent. Color of young stems: 146C. Color of mature stems: 146D with age becoming woody N199A.

Foliage description:

*General description.*—Fragrance: None detected. Form: Simple. Arrangement on flowering stem: Opposite.

*Leaves.*—Aspect: At acute angle to stem with tip turning downward. Shape: Elliptic. Margin: Entire. Apex: Broadly acute. Base: Attenuate. Venation pattern: Pinnate. Length of mature leaf: Approximately 2.5 cm. Width of mature leaf: Approximately 6.0 mm. Texture of upper and lower surfaces: Moderately glandular pubescent. Gland color: Colorless, transparent. Color of upper surface of young foliage: 137B with midvein of 146C. Color of lower surface of young foliage: Closest to 138A with midvein of 146D. Color of upper surface of mature foliage: 137A with midvein of 146C. Color of lower surface of mature foliage: 146B with midvein of 146D.

*Petiole.*—Length: Approximately 3.0 mm. Diameter: Approximately 1.0 mm. Texture: Moderately glandular pubescent. Gland color: Colorless, transparent. Color: 146D.

Flowering description:

*Flowering habit.*—'Balcaborim' is freely flowering under outdoor growing conditions with substantially continuous blooming from spring through autumn and year-round in greenhouse environment.

*Lastingness of individual flower on the plant.*—Approximately 5 to 7 days.

Flower description:

*General description.*—Type: Single, salverform. Quantity per plant: Approximately 134. Fragrance: None detected.

*Bud.*—Rate of opening: Generally takes 3 to 4 days for bud to progress from first color to fully open flower. Quantity per plant: Approximately 35.

*Bud just before opening.*—Shape: Oblong. Length: Approximately 2.0 cm. Diameter: Approximately 7.0 mm. Texture: Densely glandular pubescent. Gland color: Colorless, transparent. Color: Petal portion 174B, tube portion 154C, venation of N92A.

*Corolla.*—Diameter: Approximately 3.0 cm.

*Petals.*—Quantity: 5, fused to form a tube. Shape: Obovate. Margin: Entire. Apex: Occasionally shallowly notched. Length from tube: Approximately 1.2 cm. Length of free portion: Approximately 5.0 mm. Width: Approximately 1.2 cm. Texture of upper surface: Glabrous. Texture of lower surface: Glandular pubescent, dense along venation. Gland color: Colorless, transparent. Color of upper surface when first open: Closest to 45B with midveins of 46A. Color of lower surface when first and fully open: Closest to 174D with midveins of 59A. Color of upper surface when fully open: Closest to 34A with midveins of 44A.

*Corolla tube.*—Length: Approximately 1.5 cm. Diameter at distal end: Approximately 5.0 mm. Diameter at proximal end: Approximately 1.0 mm. Texture of inner surface: Glabrous. Texture of outer surface: Densely glandular pubescent. Gland color: Colorless, transparent. Color of inner surface: 13A with 46B at throat opening, venation of N77A. Color of outer surface: 154D with venation of N77A.

*Sepals.*—Quantity per flower: 5, fused along lower half. Shape: Lanceolate. Apex: Acute. Length: Approximately 1.0 cm. Width: Approximately 3.0 mm. Texture of upper and lower surfaces: Densely glandular pubescent. Gland color: Colorless, transparent. Color of upper surface: 137A. Color of lower surface: 138A with base of 144C.

*Peduncle.*—Strength: Strong, flexible. Aspect: Acute angle to stem. Length: Approximately 1.0 cm. Diameter: Approximately 1.0 mm. Texture: Densely glandular pubescent. Gland color: Colorless, transparent. Color: 146C.

*Reproductive organs.*—Androecium: Stamen quantity: 5, basifixed. Stamen length: Approximately 1.3 cm. Filament length of fixed portion: Approximately 5.0 mm. Filament color: 150C. Anther shape: Bilobed, ovoid. Anther length: Approximately 1.0 mm. Anther color: 8A. Pollen amount: Abundant. Pollen color: 8C. Gynoecium: Pistil quantity: 1 per flower. Pistil length: Approximately 1.0 cm. Stigma shape: Funnel. Stigma length: Less than 1.0 mm. Stigma color: 145A. Style length: Approximately 9.0 mm. Style color: 145B. Ovary diameter: Approximately 1.0 mm. Ovary color: 144A.

Seed and fruit production: Neither seed nor fruit production has been observed.

Disease and pest resistance: Resistance to pathogens and pests common to *Calibrachoa* has not been observed.

What is claimed is:

1. A new and distinct cultivar of *Calibrachoa* plant named 'Balcaborim', substantially as herein illustrated and described.

* * * * *